(12) United States Patent
Yada et al.

(10) Patent No.: US 6,448,438 B1
(45) Date of Patent: Sep. 10, 2002

(54) METHOD FOR PURIFYING ACRYLIC ACID

(75) Inventors: Shuhei Yada, Tokyo; Masahiko Yamagishi, Mie; Kouji Kasamatsu, Mie; Yasuyuki Sakakura, Mie; Kiyoshi Takahashi, Mie, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/493,011

(22) Filed: Jan. 28, 2000

(30) Foreign Application Priority Data

Jan. 29, 1999 (JP) ............................. 11-021127

(51) Int. Cl.[7] ..................... C07C 51/21; C07C 51/235
(52) U.S. Cl. ........................... 562/532; 562/545
(58) Field of Search .................... 562/532, 545

(56) References Cited

U.S. PATENT DOCUMENTS 3,988,213 A  10/1976  Yoshida et al.

FOREIGN PATENT DOCUMENTS

EP        0 695 736      2/1996

*Primary Examiner*—Paul J. Killos
*Assistant Examiner*—Taylor V. Oh
(74) *Attorney, Agent, or Firm*—Oblon, Spivak, McClelland, Maier & Neustadt, P.C.

(57) ABSTRACT

A method for purifying acrylic acid, which comprises carrying out dehydration distillation of an aqueous solution of acrylic acid by means of a dehydration column, wherein a distillation column having a theoretical plate number of at least 3 plates is used as the dehydration column, and the operational temperature of a site corresponding to the second theoretical plate is adjusted to be from 50 to 78° C.

6 Claims, 1 Drawing Sheet

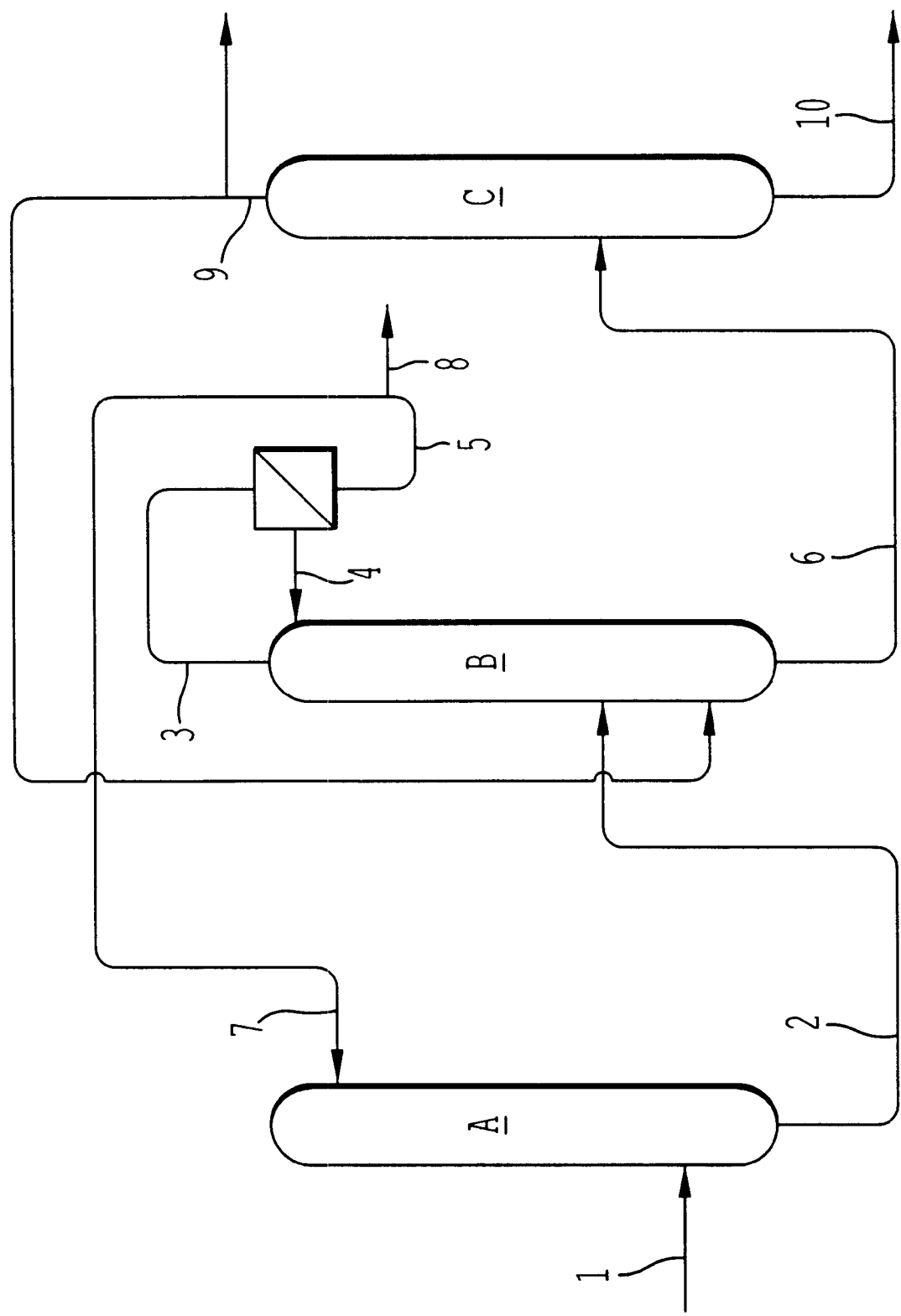

METHOD FOR PURIFYING ACRYLIC ACID

The present invention relates to a method for purifying acrylic acid. Particularly, it relates to a method for purifying acrylic acid from an aqueous solution of acrylic acid, while preventing polymerization of acrylic acid. More particularly, it relates to a method whereby an operation for purifying acrylic acid can be carried out constantly over a long period of time while preventing polymerization of acrylic acid in a distillation column at the time of removing low boiling point components such as water and acetic acid by means of a dehydration column from a crude aqueous solution of acrylic acid obtainable by catalytic oxidation of e.g. propylene.

As a typical method for producing acrylic acid, a method may be mentioned which comprises oxidizing propylene and/or acrolein by a molecular oxygen-containing gas in the presence of steam by means of an oxidizing catalyst. A crude aqueous solution of acrylic acid can be obtained by cooling and/or absorbing by water, reaction gas thus obtained. This crude aqueous solution of acrylic acid contains, in addition to acrylic acid, by-products such as acetic acid, formic acid, formaldehyde and acetaldehyde. Among these by-products, one most abundantly formed and being accordingly particularly important at the time of purification, is acetic acid. It is believed to be not so efficient to separate water, acetic acid and acrylic acid directly by distillation in view of their chemical similarity and the physicochemical properties such as gas-liquid equilibrium.

Accordingly, it has been common to employ, as a method for purifying acrylic acid, a method which comprises subjecting water to dehydration distillation by means of an organic solvent azeotropically distillable with water (which may sometimes be hereinafter referred to as "an azeotropic solvent") and further separating acetic acid by distillation. For the distillation process to carry out such separation of water and acetic acid, a method wherein both will be separated simultaneously by a single distillation column (hereinafter referred to as "a single column method") and a method wherein they are separated by means of the respective distillation columns (hereinafter referred to as "a double column method"), are conceivable, and many proposals have been made for the respective methods, as follows.
(1) With respect to the single column method JP-B-46-18967, JP-B-46-29372, JP-B-46-22456, JP-B-46-34692, JP-B-49-21124, JP-A-5-246941, etc.
(2) With respect to the double column method
JP-B-41-15569, JP-B-46-18966, JP-B-50-25451, JP-B-63-10691, JP-A-3-181440, JP-B-6-15495, JP-B-6-15496, JP-A-8-40974, etc.

These two methods have the following merits and demerits.

The single column method is intended to separate water and acetic acid simultaneously by a single distillation column, whereby it is required to employ a distillation column having a large plate number, and a large reflux ratio will be required. Accordingly, this method is disadvantageous from the viewpoint of energy. Further, as the plate number increases, the column bottom pressure tends to be high, and the column bottom temperature will accordingly be high, but it is not desirable to subject readily polymerizable acrylic acid to such a high temperature.

Whereas, in the double column method, water and acetic acid are separated by means of distillation columns respectively, whereby the optimum distillation conditions and distillation column can be employed, and this method is advantageous also from the viewpoint of energy. Further, this method has a merit such that acetic acid as the main by-product can be recovered from the distillation column for separation of acetic acid. Further, the plate number of each column can be reduced, and the column bottom temperature can be made low, hereby this method is preferred also with a view to prevention of polymerization of acrylic acid.

However, also in the process for purifying acrylic acid by this double column method, polymerization of acrylic acid has been likely to take place especially in the vicinity of the bottom of the dehydration column, whereby a stabilized operation has been still difficult.

To overcome such difficulty, JP-A-8-40974 proposes a method of controlling the concentrations of water and an azeotropic solvent in the bottom of the azeotropic dehydration column. However, this method has been still inadequate to carry out a continuous operation for a few months under a stabilized condition.

It is an object of the present invention to provide operational conditions to prevent polymerization of acrylic acid and make it possible to operate the distillation column under a stabilized condition for a long period of time, when an aqueous solution of acrylic acid is subjected to dehydration by means of a dehydration column.

The present inventors have made various studies on distillation conditions by paying a particular attention to the fact that the above-mentioned polymer of acrylic acid will deposit at a specific site, whereby a continuous operation of the dehydration column for a long period of time will be impossible. As a result, they have found it possible to present polymerization of acrylic acid in the distillation column by controlling the temperature of the specific site in the dehydration column within a specific range, and thus have arrived at the present invention.

That is, the present invention provides a method for purifying acrylic acid, which comprises carrying out dehydration of an aqueous solution of acrylic acid by means of a dehydration column, wherein a distillation column having a theoretical plate number of at least 3 plates is used as the dehydration column, and the operational temperature of a site corresponding to the second theoretical plate is adjusted to be from 50 to 78° C.

The present invention also provides the above-mentioned method for purifying acrylic acid, wherein the operational temperature of the site corresponding to the second theoretical plate is adjusted to be from 60 to 73° C., and the above-mentioned method for purifying acrylic acid, wherein the bottom temperature of the dehydration column is adjusted to be from 60 to 90° C.

Further, the present invention provides the above-mentioned method for purifying acrylic acid, wherein the aqueous solution of acrylic acid is a crude aqueous solution obtained from a reaction gas formed by catalytically oxidizing propylene and/or acrolein by molecular oxygen, and the above-mentioned method for purifying acrylic acid, wherein the acrylic acid concentration of the aqueous solution of acrylic acid is at least 40 wt %.

Furthermore, the present invention provides the above-mentioned method for purifying acrylic acid, wherein an organic solvent azeotropically distillable with water is used at the time of the dehydration distillation.

In the accompanying drawing, FIG. 1 is a flow sheet illustrating a process for purifying acrylic acid, which can be applied to the method of the present invention.

Now, the present invention will be described in detail with reference to the preferred embodiments.
(1) The aqueous solution of acrylic acid.

The aqueous solution of acrylic acid to be treated by the present invention, is not particularly limited. However, it is most effective to apply the present invention to a crude aqueous solution of acrylic acid obtained by cooling and/or absorbing in water a reaction gas formed by catalytic oxidation of propylene and/or acrolein by means of molecular oxygen.

The present invention will be described with reference to a case wherein a crude aqueous solution of acrylic acid thus obtained, will be purified.

As mentioned above, the crude aqueous solution of acrylic acid obtainable by the catalytic oxidation of e.g. propylene, contains by-products, such as acetic acid, formic acid, formaldehyde and acetaldehyde, in addition to acrylic acid as the desired substance.

When the conversion in the above-mentioned oxidation reaction is high, the method of the present invention may be applied directly to the crude aqueous solution of acrylic acid thus obtained. However, in a case where the conversion is low, unreacted acrolein will be included in the aqueous solution, and it is advisable to preliminarily remove such acrolein by e.g. stripping.

(2) Process for purifying acrylic acid

The process to which the method of the present invention is applied, is preferably a process of the double column method employing a dehydration column and an acetic acid separation column, as mentioned above. A flow sheet of an example of such a process is shown in FIG. 1.

Now, the process will be described with reference to this flow sheet.

A reaction product gas obtained by catalytically oxidizing propylene and/or acrolein by a molecular oxygen-containing gas by means of an oxidation catalyst in the presence of steam, is introduced by a pipeline 1 into an acrylic acid absorption column (A) and contacted with an absorbing liquid composed mainly of water, which is introduced by a pipeline 7 to absorb acrylic acid, whereby a crude aqueous solution of acrylic acid can be obtained as the bottom (a pipeline 2) from the acrylic acid absorption column. Usually, in order to improve the efficiency for absorption of acrylic acid, part of the bottom of the pipeline 2, is cooled and recycled to the acrylic acid absorption column (not shown) in many cases. As the absorbing liquid, it is preferred to employ the distillate from the dehydration column, with a view to reducing the amount of waste water.

This crude aqueous solution of acrylic acid may contain, in addition to acrylic acid, by-products of the oxidation reaction, such as acetic acid, formic acid and formaldehyde, and unreacted acrolein. Accordingly, the aqueous solution may be supplied to an acrolein stripping columns to remove acrolein as the case requires (not shown).

The crude aqueous solution of acrylic acid as the bottom from the acrylic acid absorption column, is introduced into a dehydration column (B) by a pipeline 2. In the dehydration column, an azeotropic solvent may be introduced from a pipeline (not shown) as the case requires, and a column top gas comprising an azeotropic solvent, water and part of acetic acid, is generated from the column top by the (azeotropic) dehydration, and this gas is cooled to obtain a column top distillate. This distillate is subjected to phase separation, whereupon the azeotropic solvent phase is refluxed via a pipeline 4, and most of the aqueous phase is reused (a pipeline 7) as a liquid for absorbing the oxidation reaction gas of the acrylic acid absorption column, while a part of the aqueous phase may be discharged out of the system (a pipeline 8) for the balance of water. The concentration of water in the bottom of the dehydration column can be controlled by the amount of reflux of the azeotropic solvent. The amount of reflux of the azeotropic solvent is determined depending upon the azeotropic composition of water and the azeotropic solvent, and it is preferred to carry out the operation so that the concentration of water in the bottom is maintained to be at most 1 wt %, and the concentration of the azeotropic solvent is preferably controlled to be at most 40 wt %.

The bottom from the dehydration column is supplied via a pipeline 6 into an acetic acid separation column (C). Here, substantially all low boiling point impurities are removed, and purified acrylic acid is obtainable as the bottom (a pipeline 10). The purified acrylic acid can be employed in the subsequent step (not shown) as a material for an acrylic acid ester. A distillate (a pipeline 9) consisting essentially of acetic acid, the azeotropic solvent and acrylic acid, obtained from the top of the acetic acid separation column, is usually recycled to the dehydration column to recover the contained acrylic acid.

When the distillate from the acetic acid separation column is recycled to the dehydration column, the feeding position to the dehydration column is also of importance. Usually, an optimum feeding plate is present depending upon the concentration ratio of acetic acid and acrylic acid. However, because of the structural similarity, acetic acid and acrylic acid tend to be more hardly separable by distillation than assumed from the difference in their boiling points, and in many cases, the distillate from the acetic acid separation column contains a substantial amount of acrylic acid. In the process for producing acrylic acid, purified acetic acid may be separated by equipments separately provided for separation and recovery of acetic acid prior to recycling the distillate from the acetic acid separation column to the dehydration column, and a liquid comprising acrylic acid and the azeotropic solvent, as the main components, may be recycled.

(3) Dehydration column

In the present invention, as the dehydration column, one having a theoretical plate number of at least 3 plates, is used. The upper limit of the theoretical plate number is not particularly limited. However, taking into consideration the equipment costs, etc., it is common to employ one having at most 50 theoretical plates. More preferably, the theoretical plate number is from 5 to 20 plates.

The dehydration column to be used in the present invention, is not particularly limited with respect to the type, and a plate column or a packed column may, for example, be employed. In the case of a plate column, from 10 to 50 trays will usually be employed to provide the above-mentioned preferred theoretical plate number. In the present invention, the operation temperature of the site corresponding to the second theoretical plate, which corresponds to the stripping section of the dehydration column, is adjusted to be within a specific range of from 50 to 78° C.

The operational pressure of the dehydration column is usually such that the column top pressure is adjusted to be a reduced pressure of e.g. from 100 to 300 mmHg-abs, in order not to expose acrylic acid to a high temperature.

Trays or packing materials for the dehydration column suitable for application of the method of the present invention, are preferably ones having a small pressure difference and high efficiency, and from the viewpoint of distillation of a substance which is readily polymerizable, they are preferably ones having a simple structure with little protrusions or the like.

Such tray or packing materials may specifically be, for example, sieve tray, dual-flow tray or ripple tray, and as packing materials, IMTP (interlocks metal tower packing, manufactured by Norton Co.), CMR (cascade mini ring, manufactured by Dodwel Marketing Co.) or Melapack (manufactured by Sumitomo Heavy Industries, Ltd.). However, useful trays or packing materials are not limited to such specific examples.

(4) Temperature of the site corresponding to the second theoretical plate and method for controlling it In the present invention, the temperature of the site corresponding to the second theoretical plate is adjusted to be from 50 to 78° C., as mentioned above.

If the temperature exceeds this range, a polymer of acrylic acid tends to form and accumulate inside the dehydration column, and it becomes difficult to carry out the operation under a stabilized condition over a long period of time for practical industrial operation.

If the temperature is lower than this range, the evaporation rate tends to be low, and an installation for reduced pressure tends to be required to be large, or the retention time in the column tends to be long, or the capacity of the distillation column itself will be required to be large.

More preferably, the operational temperature of the site corresponding to the second theoretical plate is from 60 to 73° C.

In a distillation column, the theoretical plate number is counted from the bottom of the column, and accordingly, the site corresponding to the second theoretical plate, corresponds to the position of the tray or the packing material corresponding to the theoretical plate next to the reboiler (first theoretical plate) at the bottom of the column.

In the case of a tray column, the tray efficiency differs depending upon the type of trays, the substance to be distilled, etc., and the actual tray number corresponding to the first theoretical plate, is usually from 2 to 5 trays. When a plurality of actual trays correspond to the first theoretical plate, in the present invention, as "the temperature of the theoretical plate", the temperature of the top tray among the corresponding actual trays, will be used.

For example, when trays having a tray efficiency of 25% are used, the first theoretical plate corresponds to an actual tray number of 4 trays. In this case, "the temperature of the second theoretical plate" means the temperature of the 4th tray from the column bottoms.

In the case of the packing material, when the packing height corresponding to the first theoretical plate is "h", the temperature at the position of "1h" from the bottom of the packing, corresponds to "the temperature of the second theoretical plate" (as the reboiler at the column bottom corresponds to the first plate).

Further, the temperature at the bottom of the dehydration column is adjusted usually within a range of from 60 to 90° C., preferably from 65 to 86° C. If this temperature exceeds 90° C., a polymer of acrylic acid tends to form at the bottom of the column. On the other hand, if it is lower than 60° C., there will be economical disadvantages from the equipment and operational aspects, such as a decrease in the evaporation rate.

Further, when a polymerization inhibitor is supplied to the dehydration column as will be described hereinafter, formation of a polymer at the bottom of the column will be suppressed substantially by the effects of the polymerization inhibitor. However, by adjusting the temperature of the second theoretical plate to the above range, it is possible to control the temperature of the vapor generated from the bottom of the column, and accordingly, it is possible to prevent polymerization at the lowermost portion of trays where no polymerization inhibitor is present.

The conditions of the present invention are preferably maintained from the initiation of the operation of the dehydration column. It is not advisable to change the conditions during the operation to the conditions of the present invention or to depart from the conditions of the present invention and again return to the conditions of the present invention, during the operation, since it is difficult to suppress the polymerization-accelerating effect by a polymer formed during the period wherein the operational conditions are outside the conditions of the present invention, although some effects by the present invention may be obtained. For a continuous operation for a long period of time i.e. for at least one month, it is important that the time of departure from the conditions of the present invention should be within 120 hours. If the departing time exceeds this range, a polymer of acrylic acid tends to form and accumulate in the dehydration column, such being undesirable.

The temperature of the second theoretical plate may be controlled within the range of the present invention by ascertaining the interrelation between the temperature of the bottom of the distillation column and the temperature of the second theoretical plate experimentally by e.g. simulation by means of a computer, and controlling the temperature of the bottom of the column based thereon.

Further, at that time, it is advisable to employ a method of watching so that the temperature will not depart from the predetermined temperature range by providing a thermometer at the site corresponding to the second theoretical plate.

As a method for controlling the temperature of the bottom of the column, it is simplest to change the heating load of the reboiler, but a method of supplying e.g. an azeotropic solvent into the dehydration column from e.g. the bottom of the column, may be employed.

In the process for purifying acrylic acid, to which the method of the present invention is applied, the following process for recovery of energy or recovery of the product may, for example, be incorporated without any particular restriction, so long as it does not hinder the object or the effects of the present invention.

(a) A part or all of the distillate from the top of the acetic acid separation column is recycled to the dehydration column.

(b) A part or all of the distillate from the top of the dehydration column is reused as absorbing water for the acrylic acid absorption column (the obtained crude aqueous solution of acrylic acid will be supplied to the dehydration column).

(c) In order to reuse the polymerization inhibitor contained in the bottom of the dehydration column, a part of the bottom is recycled to the dehydration column.

(5) Azeotropic solvent and polymerization inhibitor.

In the method for purifying acrylic acid according to the present invention, it is preferred to employ an organic solvent (an azeotropic solvent) azeotropically distillable with water, in order to carry out dehydration efficiently.

The azeotropic solvent which can be employed in the present invention, may, for example, be toluene, heptane, cyclohexane, methylcyclohexane or isobutyl ether, which is azeotropically distillable with water and acetic acid, or n-butyl acetate, isobutyl acetate, isopropyl acetate or methyl isobutyl ketone, which is azeotropically distillable with water although not azeotropically distillable with acetic acid. These solvents may be used alone or in combination as a mixture of two or more of them. In the present invention, the type of the azeotropic solvent is not particularly limited.

The azeotropic solvent usually serves as a diluting agent for acrylic acid. Accordingly, from the viewpoint of preventing of polymerization, the concentration of the azeotropic solvent in the dehydration column or in the bottom should better be high, but the concentration may be determined based on the balance with the energy load required for distillation.

Further, in the method of the present invention, it is preferred to incorporate a polymerization inhibitor in the bottom of the distillation column in order to prevent polymerization of acrylic acid.

The polymerization inhibitor which can be used for the method of the present invention, is not particularly limited. For example, a polymerization inhibitor of a phenol type such as hydroquinone, hydroquinone monomethyl ether or phenothiazine, of an amine type or of a copper type such as copper acetate, may be employed.

Such a polymerization inhibitor may be supplied from the top of the column and/or from the liquid-feeding plate for distillation, together with acrylic acid, the azeotropic solvent, water and/or a mixture thereof. As is well known, oxygen also serves as a radical polymerization inhibitor, and accordingly, a method of blowing a gas containing molecular oxygen, from the bottom of the distillation column, may also be employed.

By employing the method of the present invention, it has been made possible to effectively prevent polymerization of acrylic acid in a dehydration column for the process for purifying acrylic acid and to carry out the operation under a stabilized condition over a long period of time.

Now, the method of the present invention will be described in further detail with reference to Examples and Comparative Examples. However, it should be understood that the present invention is by no means restricted to such specific Examples.

EXAMPLE 1

30 Ripple trays were provided in a distillation column with a diameter of 1,000 mm having a reboiler at the bottom and a condenser at the top, the outlet of this condenser being connected to a vacuum apparatus. (The trays are numbered 1st, 2nd . . . from the column bottom side, so that the tray closest to the column top is called a 30th tray.) The 30 trays correspond to a theoretical plate number of 9 plates. (Accordingly, the distillation column corresponds to a theoretical plate number of 10 plates including the reboiler which corresponds to one plate.)

The aqueous solution of acrylic acid (hereinafter referred to as liquid (A)) used as the starting material liquid for distillation contained 55 wt % of acrylic acid, 1.5 wt % of acetic acid, 0.3 wt % of formaldehyde and a small amount of formic acid.

The operation of the dehydration column was carried out by using toluene as the azeotropic solvent.

Firstly, the distillation column was stabilized by using toluene, and then liquid (A) was supplied to the 16th tray at a rate of 1,100 kg per hour, and toluene was supplied to the 30th tray at a rate of 3,100 kg per hour. The column top pressure was controlled to be 105 mmHg, and from the column top, hydroquinone and phenothiazine were supplied as polymerization inhibitors. The feeding amounts were adjusted so that the concentrations of the polymerization inhibitors in the bottom would be 800 ppm of hydroquinone and 500 ppm of phenothiazine. To the column bottom, air was supplied at a rate of 500 l per hour.

The distillate condensed by the condenser at the column top was left to stand and separated by a decanter, and then the azeotropic solvent phase was refluxed in the entire amount, and the aqueous phase was withdrawn. As the heating source for the reboiler, steam having a pressure of 2 kg/cm$^2$·G was used.

In this manner, this dehydration column was continuously operated for 3 months by adjusting the temperature of the third tray (the second theoretical plate) to 71° C., the temperature of the bottom to 83° C. and the column top temperature to 44° C.

The composition of the bottom withdrawn from the column bottom during the operation contained in addition to acrylic acid, 2.3 wt % of acetic acid, 0.6 wt % of water, 15 wt % of toluene and the polymerization inhibitors.

3 Months later, the operation was stopped, and the distillation column was opened and inspected, whereby no polymer of acrylic acid was detected.

EXAMPLE 2 and 3 and COMPARATIVE EXAMPLE 1

Experiments of dehydration distillation were carried out in the same manner as in Example 1 except that the column top pressure in Example 1 was changed as shown in Table 1. The results of the operations are shown in Table 1 together with the temperatures of the third tray (the second theoretical plate) and the bottom.

TABLE 1

|  | Example 2 | Example 3 | Comparative Example 1 |
|---|---|---|---|
| Azeotropic solvent | Toluene | Toluene | Toluene |
| Column top pressure (mmHg) | 115 | 140 | 150 |
| Temperature of the bottom (° C.) | 83 | 89 | 92 |
| Temperature of 3rd tray (° C.) | 71 | 76 | 80 |
| Operation period | 6 months | 3 months | 2.5 months |
| Operation state | Normal | Normal | ΔP of the distillation column gradually increased, and it became impossible to continue the operation |
| Inspection results of the distillation column | No polymer observed | A small amount of a polymer was observed on the 2nd tray | A substantial amount of a polymer was observed on the 1st to 4th trays |

ΔP: Pressure difference

EXAMPLES 4 to 7 and COMPARATIVE EXAMPLE 2

Dehydration distillation was carried out in the same manner as in Example 1 except that in Example 1, the type of the azeotropic solvent and the column top pressure were changed as shown in Table 2. The results of operations are shown in Table 2 together with the temperature of the third tray (second theoretical plate) and the bottom.

TABLE 2

|  | Example 4 | Example 5 | Example 6 | Example 7 | Comparative Example 2 |
|---|---|---|---|---|---|
| Azeotropic solvent | Toluene | Methyl isobutyl ketone | Methyl isobutyl ketone | Isobutyl acetate | Isobutyl acetate |
| Column top pressure (mmHg) | 105 | 100 | 120 | 110 | 160 |
| Temperature of the bottom (° C.) | 84 | 82 | 86 | 85 | 94 |
| Temperature of 3rd tray (° C.) | 72 | 71 | 73 | 72 | 82 |
| Operation period | 3 months | 3 months | 3 months | 3 months | 1 month |
| Operation state | Normal | Normal | Normal | Normal | ΔP of the distillation column started to increase, and the operation was stopped |
| Inspection results of the distillation column | No polymer observed | No polymer observed | No polymer observed | No polymer observed | A polymer was observed on trays at the lower portion of the column |

ΔP: Pressure difference

EXAMPLE 8

The trays were removed from the distillation column used in Example 1, and Melapack (manufactured by Sumitomo Heavy Industries, Ltd.) was packed. Dehydration distillation was carried out in the same manner as in Example 1 except for the above condition. The results of the operation are shown in Table 3 together with the temperature of the site corresponding to the second theoretical plate and the temperature of the bottom.

TABLE 3

|  | Example 8 |
|---|---|
| Azeotropic solvent | Toluene |
| Column top pressure (mmHg) | 145 |
| Temperature of the bottom (° C.) | 83 |
| Temperature of the site corresponding to the second theoretical plate (° C.) | 70 |
| Operation period | 3 months |
| Operation state | Normal |

Evaluation of the results

From the above Examples 1 to 7, it is evident that when the distillation operation is carried out by the method of the present invention, the operation can be continued under a stabilized condition for at least 3 months and for 6 months at the longest.

On the other hand, in Comparative Examples 1 and 2 wherein the temperature of the second theoretical plate became outside the range of the present invention, the pressure difference rose to such an extent that the operation could not be continued, in one month or 2.5 months.

Further, in the operation employing a packed column, it has been believed that industrial practical operation is difficult due to disturbance of the gas-liquid dispersion in the packed column due to formation of a polymer. However, by employing the method of the present invention, formation of the polymer can be controlled, and the operation using a packed column can be carried out in the same manner as usual distillation.

What is claimed is:

1. A method for purifying acrylic acid, which comprises carrying out dehydration distillation of an aqueous solution of acrylic acid by means of a dehydration column, wherein a distillation column having a theoretical plate number of at least 3 plates is used as the dehydration column, and the operational temperature of a site corresponding to the second theoretical plate is adjusted to be from 50 to 78° C.

2. The method for purifying acrylic acid according to claim 1, wherein the operational temperature of the site corresponding to the second theoretical plate is adjusted to be from 60 to 73° C.

3. The method for purifying acrylic acid according to claim 1, wherein the bottom temperature of the dehydration column is adjusted to be from 60 to 90° C.

4. The method for purifying acrylic acid according to claim 1, wherein the aqueous solution of acrylic acid is a crude aqueous solution obtained from a reaction gas formed by catalytically oxidizing propylene and/or acrolein by molecular oxygen.

5. The method for purifying acrylic acid according to claim 1, wherein the concentration of the aqueous solution of acrylic acid is at least 40 wt %.

6. The method for purifying acrylic acid according to claim 1, wherein an organic solvent azeotropically distillable with water is used at the time of the dehydration distillation.

* * * * *